United States Patent
Wiederin (10) Patent No.: US 10,302,571 B2
(45) Date of Patent: May 28, 2019

(54) INTERCHANGEABLE, VISUALLY MARKED SAMPLE INTRODUCTION SYSTEM MOUNTING STRUCTURE AND COMPONENTS FOR INDUCTIVELY COUPLED PLASMA SYSTEMS

(71) Applicant: Elemental Scientific, Inc., Omaha, NE (US)

(72) Inventor: Daniel R. Wiederin, Omaha, NE (US)

(73) Assignee: ELEMENTAL SCIENTIFIC, INC., Omaha, NE (US)

(*) Notice: Subject to any disclaimer, the term of this patent is extended or adjusted under 35 U.S.C. 154(b) by 343 days.

(21) Appl. No.: 15/203,457

(22) Filed: Jul. 6, 2016

(65) Prior Publication Data

US 2017/0010216 A1    Jan. 12, 2017

Related U.S. Application Data

(60) Provisional application No. 62/189,172, filed on Jul. 6, 2015.

(51) Int. Cl.
*G01N 21/73* (2006.01)
*G01N 21/71* (2006.01)
*H01J 49/04* (2006.01)

(52) U.S. Cl.
CPC .......... *G01N 21/73* (2013.01); *G01N 21/714* (2013.01); *H01J 49/04* (2013.01)

(58) Field of Classification Search
CPC ....... G01N 21/73; G01N 21/714; H01J 49/04; H01J 49/105
See application file for complete search history.

(56) References Cited

U.S. PATENT DOCUMENTS

| | | | |
|---|---|---|---|
| 5,361,904 A * | 11/1994 | Kapec | G09F 3/00 206/459.5 |
| 5,925,266 A | 7/1999 | Gagne | |
| 7,064,812 B2 * | 6/2006 | Ludviksson | G01N 21/64 250/282 |
| 8,551,401 B1 * | 10/2013 | Wiederin | G01N 33/00 422/400 |
| 8,925,375 B1 | 1/2015 | Wiederin | |
| 2010/0168561 A1 | 7/2010 | Anderson | |
| 2013/0267809 A1 | 10/2013 | Brister et al. | |

(Continued)

FOREIGN PATENT DOCUMENTS

WO    9944044 A1    9/1999

OTHER PUBLICATIONS

International Search Report and Written Opinion dated Oct. 20, 2016 for PCT/US2016/041146.

(Continued)

*Primary Examiner* — Kara E. Geisel
*Assistant Examiner* — Maurice C Smith
(74) *Attorney, Agent, or Firm* — Kevin E. West; Advent, LLP (57) ABSTRACT

A system can include an exchangeable mounting structure having a visual marking or coloring and at least one physically associated sample introduction system component having an indicating mark or color matching the visual marking or coloring of the exchangeable mounting structure. The visual marking or colored corresponds to a sample analysis configuration for analyzing a particular sample type at an analytical instrument.

18 Claims, 7 Drawing Sheets

(56) References Cited

U.S. PATENT DOCUMENTS

2014/0318274 A1* 10/2014 Zimmerman .......... B01D 15/14
73/863
2016/0233632 A1* 8/2016 Scruggs ............. H01R 13/2421

OTHER PUBLICATIONS

International Preliminary Report on Patentability dated Jan. 18, 2018 for PCT/US2016/041146.

* cited by examiner

INTERCHANGEABLE, VISUALLY MARKED SAMPLE INTRODUCTION SYSTEM MOUNTING STRUCTURE AND COMPONENTS FOR INDUCTIVELY COUPLED PLASMA SYSTEMS

CROSS-REFERENCE TO RELATED APPLICATIONS

The present application claims the benefit under 35 U.S.C. § 119(e) of U.S. Provisional Application Ser. No. 62/189,172, filed Jul. 6, 2015, and titled "INTERCHANGEABLE, VISUALLY MARKED SAMPLE INTRODUCTION SYSTEM MOUNTING STRUCTURE AND COMPONENTS FOR INDUCTIVELY COUPLED PLASMA SYSTEMS." U.S. Provisional Application Ser. No. 62/189,172 is herein incorporated by reference in its entirety.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

A system can include an exchangeable mounting structure having a visual marking or coloring and at least one physically associated sample introduction system component having an indicating mark or color matching the visual marking or coloring of the exchangeable mounting structure. The visual marking or colored corresponds to a sample analysis configuration for analyzing a particular sample type at an analytical instrument.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures.

DETAILED DESCRIPTION

Overview

ICP and ICPMS instruments can use sample introduction system configurations that have physically different components to optimize the analysis of different types of samples. For example, the configuration of the sample introduction system to analyze an environmental water sample can differ from the configuration of the sample introduction system used for the analysis of a volatile petrochemical distillate, even using the same ICP spectrometer. Some of the components of the sample introduction system may include the torch, injector, spray chamber, nebulizer, gas connections, and sample inlet line, and can include autosampler probes and other components. For example, other components of the sample introduction system can include pump systems, such as a sample pump, pump components, tubing, and valves.

At least some of the components of the sample introduction system are mounted to a mounting structure which holds the sample introduction system components relative to each other and collectively relative to the ICP or ICPMS instrument. When the sample introduction system is changed, such as for analyzing a different type of sample, the corresponding operating parameters of the ICP or ICPMS instrument, such as RF power, torch position, carrier gas flows (e.g., Argon gas flows), spray chamber temperature, sample flow rate, optical or ion optical lens settings, and the like may need to be changed to optimize the performance of the new sample introduction system configuration for the new type of sample. When the sample introduction system is changed sometimes only one or a few components need to change, for example changing only the injector size or material comprising one or more of the components (e.g., changing between a quartz injector, a platinum injector, a sapphire injector, etc.). In other cases all or nearly all components will change. Therefore there are some components which can be common among the various optimal sample introduction systems.

Since many ICP emission spectrometers or ICP mass spectrometer instruments can used to analyze several different types of samples, the sample introduction system may need to be changed often. It is also possible that sample introduction system components can be accidentally and erroneously mixed among various configurations, such as during cleaning the sample introduction system components, during storage of the sample introduction system components, during transport of the sample introduction system components between differing analysis instruments, and so forth. Such mixing among the various configurations of the sample introduction system components can lead to unknown effects on the operation of the instrument, which can introduce error into subsequent sample analyses, where the origin of the particular error may not readily be identifiable. Further for a particular type of sample analysis it is desirable that methods and settings for analyzing the sample can be transferred among ICP or ICPMS instruments located in laboratories around the world operated by analysts who may communicate in a variety of languages. In some cases the differences among components of the sample introduction system for the ICP or ICPMS instruments are not easily distinguished except by an expert instrument operator. Thus barriers in communicating nuances across multiple languages and varying levels of instrumentation experience among laboratory staff can present challenges in ensuring proper sample introduction system components are utilized for the appropriate sample analyses.

Accordingly, systems are described that utilize interchangeable, visually marked sample introduction system mounting structures and components for ICP or ICPMS instruments. Such systems can incorporate visually distinguishable system to mark both the mounting structure and sample introduction system components associated with the mounting structure so that laboratories can easily determine that the correct components are being used for the desired application. In an implementation, a system includes an exchangeable mounting structure having a visual marking or coloring and at least one physically associated sample introduction system component having an indicating mark or color matching the visual marking or coloring of the exchangeable mounting structure.

Example Implementations

Figure 1:
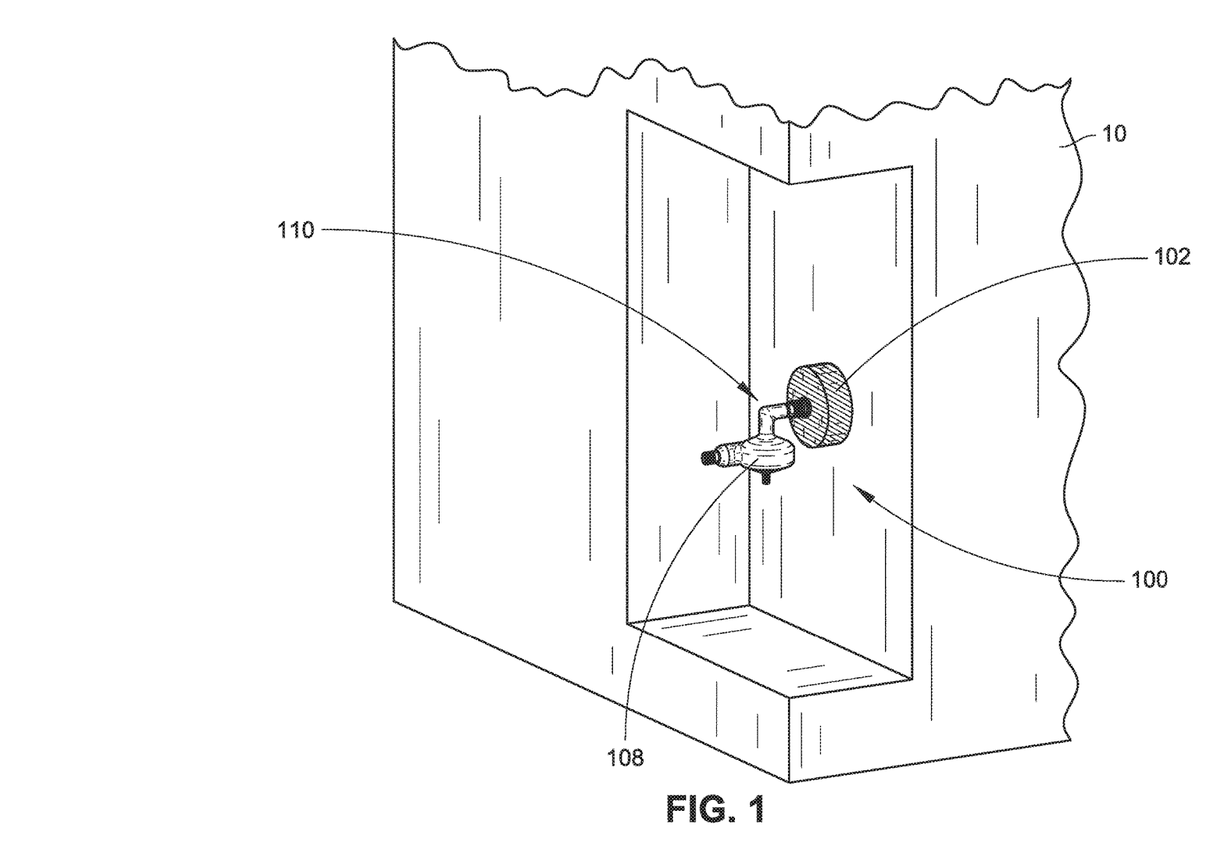
FIG. 1 is a partial isometric view of a system for managing differing sample introduction system components with respect to a mounting structure for ICP and ICPMS instruments in accordance with an example embodiment of the present disclosure.

Referring generally to FIGS. 1 through 5, example systems 100 configured to match physically associated sample introduction system mounting structures and components for ICP or ICPMS instruments are described. A system includes an exchangeable mounting structure 102 configured to couple with an ICP or ICPMS instrument (shown generally in FIG. 1 as 10). As used herein, the term "exchangeable" can refer to a removably mountable mounting structure that is configured to be mounted to an ICP or ICPMS instrument, such that one or more exchangeable mounting structures can be utilized with a single ICP or ICPMS instrument via exchange or removal of one exchangeable mounting structure and mounting of another exchangeable mounting structure. In general, the exchangeable mounting structure is configured to maintain one or more sample introduction system components in a fixed positional relationship relative to one another while coupled to the ICP or ICPMS instrument 10. In implementations, the sample introduction system components can include, but are not limited to, a torch (torches 104A and 104C are shown in FIGS. 2A through 2C), an injector (injectors 106A, 106B, 106C are shown in FIGS. 2A through 2C), a spray chamber (spray chamber 108 is shown in FIG. 1; spray chambers 108A, 108B, 108C are shown in FIGS. 2A through 2C), a nebulizer, one or more gas connections, a sample inlet line, one or more autosampler probes, one or more pump systems, a sample pump, one or more pump components, tubing, and one or more valves. Such sample introduction system components can condition a liquid sample for introduction to and analysis in the ICP or ICPMS instrument.

Figure 2A:
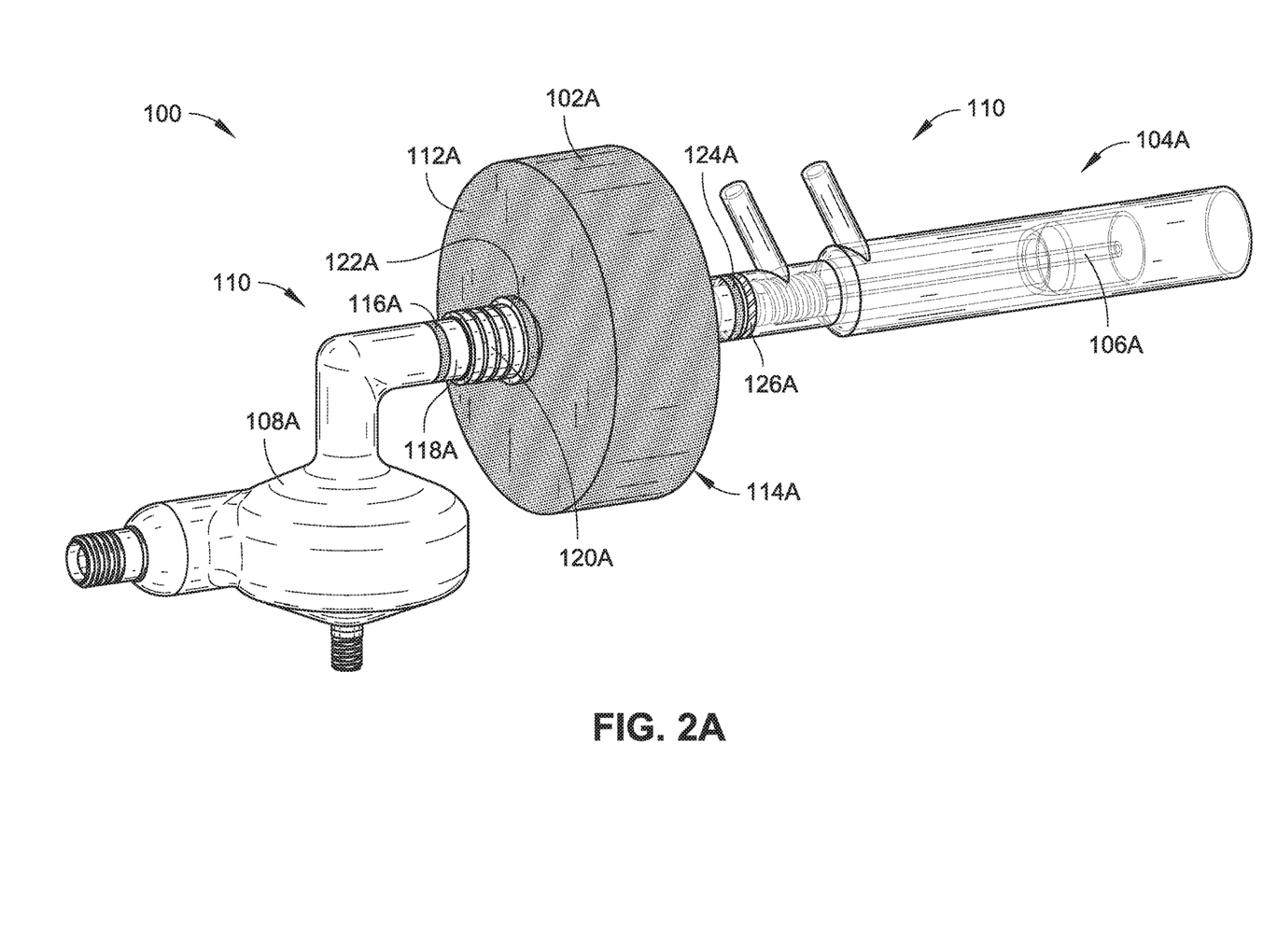
FIG. 2A is an isometric view of a system for managing differing sample introduction system components with respect to a plurality of mounting structures for ICP and ICPMS instruments in accordance with an example embodiment of the present disclosure.
Figure 2B:
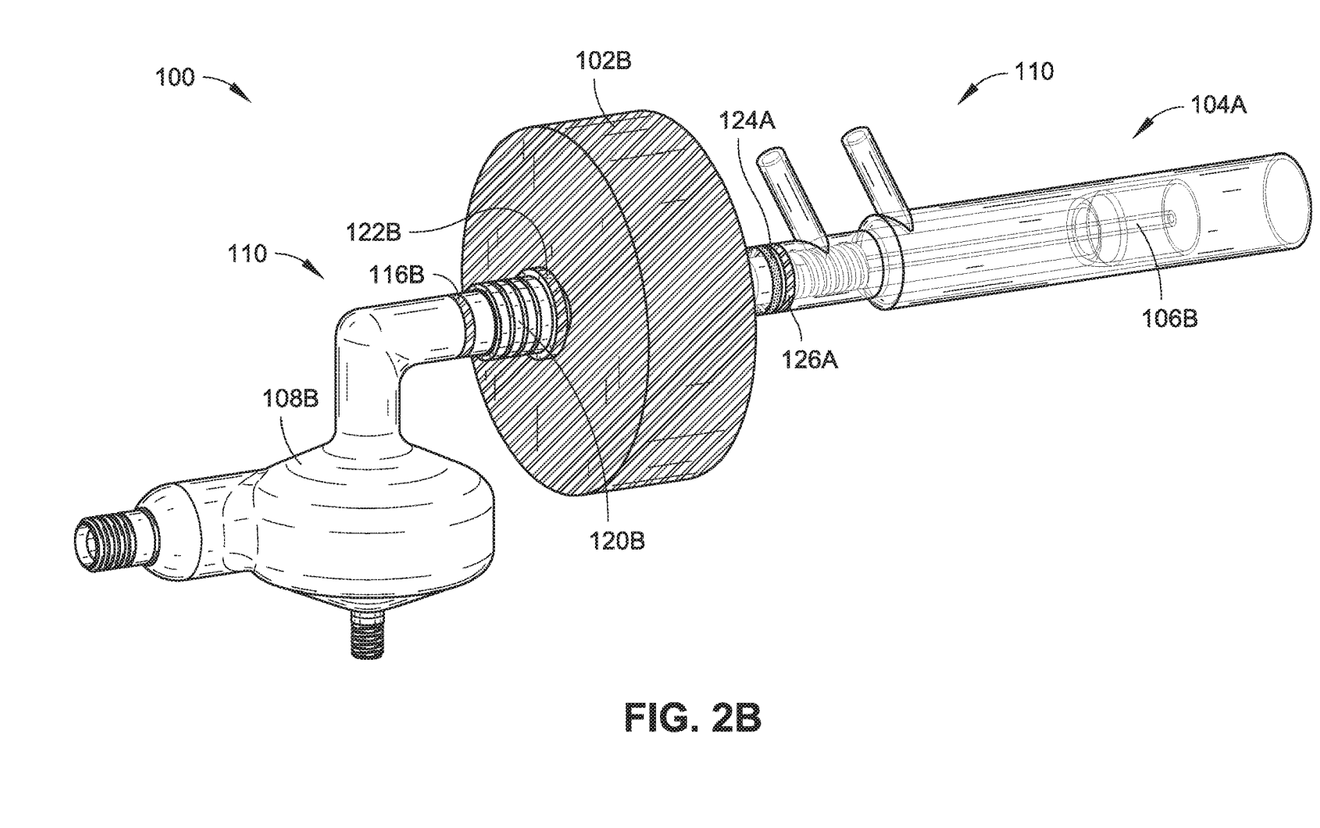
FIG. 2B is an isometric view of a system for managing differing sample introduction system components with respect to a plurality of mounting structures for ICP and ICPMS instruments in accordance with an example embodiment of the present disclosure.
Figure 2C:
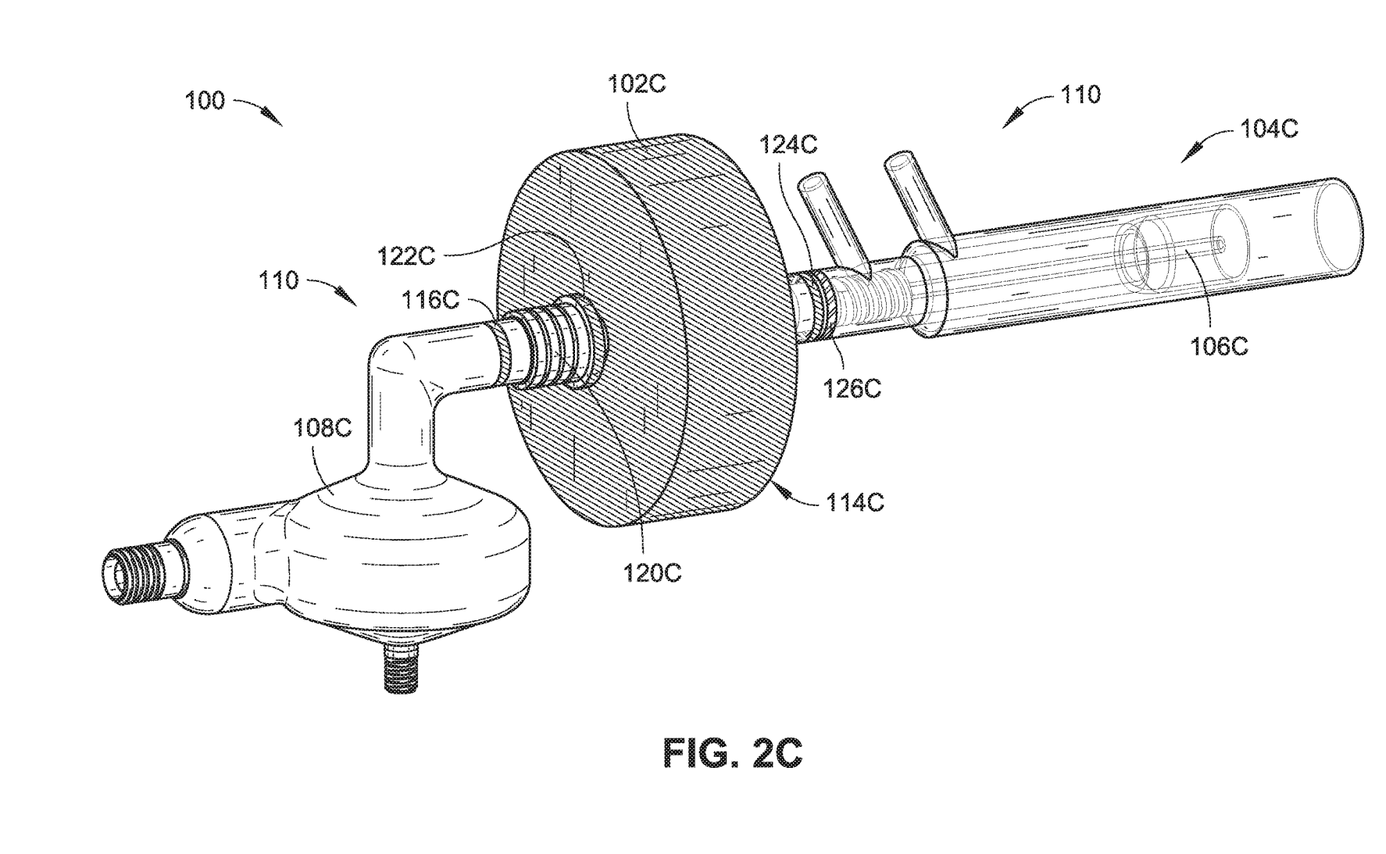
FIG. 2C is an isometric view of a system for managing differing sample introduction system components with respect to a plurality of mounting structures for ICP and ICPMS instruments in accordance with an example embodiment of the present disclosure.

In implementations, the exchangeable mounting structure 102 includes a visual marking or coloring. For example, the visual marking can include, but is not limited to, a barcode (e.g., a 2-dimensional (2-D) or matrix barcode), a letter, a number, a symbol, an alphanumeric character, a physical texture pattern, a visual pattern (e.g., color pattern), and the like. The visual marking or coloring can provide a distinguishable mechanism to identify the exchangeable mounting structure 102, particularly with reference to differing exchangeable mounting structures that can include differing visual markings or colorings. With reference to FIGS. 2A through 2C, three distinguishable exchangeable mounting structures are shown as 102A (FIG. 2A), 102B (FIG. 2B), and 102C (FIG. 2C), where each mounting structure includes a different visual marking or coloring. For example, the exchangeable mounting structure 102A includes a first visual marking or coloring (e.g., a brown coloring scheme), the exchangeable mounting structure 102B includes a second visual marking or coloring (e.g., a green coloring scheme), and the exchangeable mounting structure 102C includes a third visual marking or coloring (e.g., a blue coloring scheme). In implementations, the system 100 also includes at least one physically associated sample introduction system component 110 having an indicating mark or color matching the visual marking or coloring of the exchangeable mounting structure. In general, a sample introduction system component 110 is physically associated with a respective exchangeable mounting structure 102 when the sample introduction system component 110 is configured to be physically supported by the exchangeable mounting structure 102 when mounted to an ICP or ICPMS instrument 10. In implementations, a sample introduction system component 110 is physically associated with a respective exchangeable mounting structure 102 when the sample introduction system component 110 and the exchangeable mounting structure 102 are designed to be utilized together for a particular analysis in the ICP or ICPMS instrument 10. For example, in an implementation the exchangeable mounting structure 102A physically supports the spray chamber 108A proximate a front side 112A of the exchangeable mounting structure 102A and physically supports the torch 104A and the injector 106A proximate an instrument side 114A of the exchangeable mounting structure 102A in a sample analysis configuration for the analysis of an environmental water sample, whereas analysis of a volatile petrochemical distillate may require a different configuration of exchangeable mounting structure 102 and sample introduction system components 110, for example, utilizing the exchangeable mounting structure 102C which physically supports the spray chamber 108C proximate a front side 112C of the exchangeable mounting structure 102C and physically supports the torch 104C and the injector 106C proximate an instrument side 114C of the exchangeable mounting structure 102C.

Figure 3A:
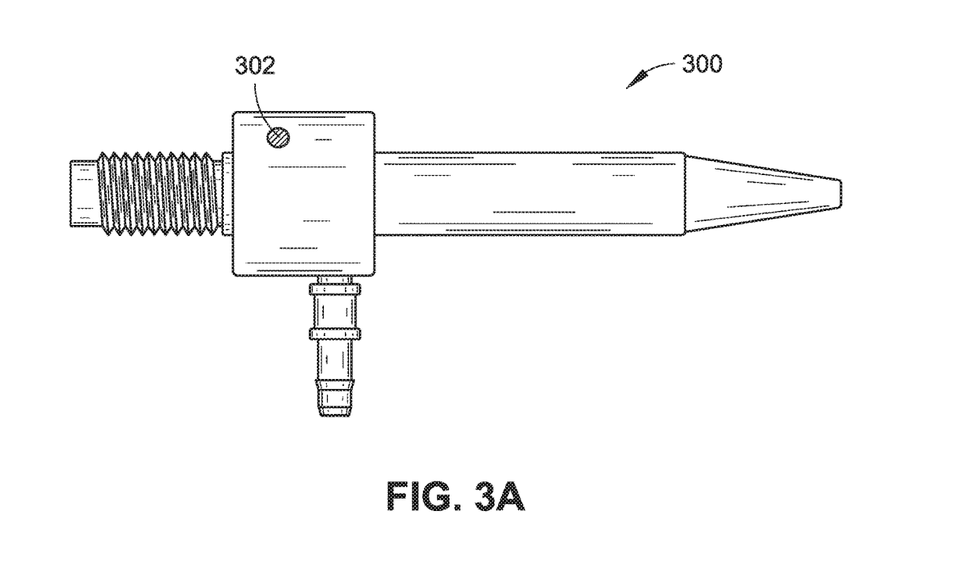
FIG. 3A is a side view of a sample introduction system component including a visual marking in accordance with an example embodiment of the present disclosure.
Figure 3B:
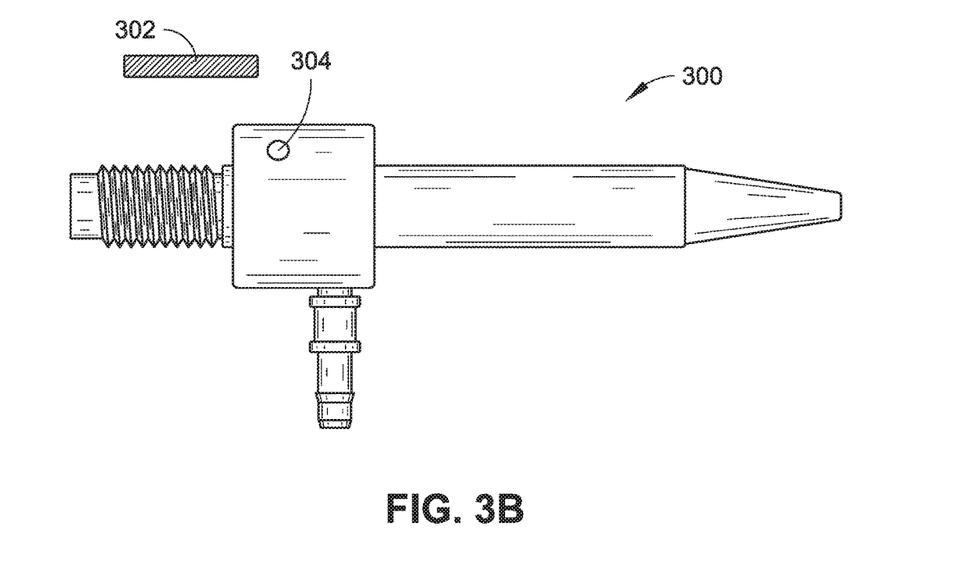
FIG. 3B is a side view of a sample introduction system component including a visual marking displaced from an aperture in accordance with an example embodiment of the present disclosure.
Figure 4:
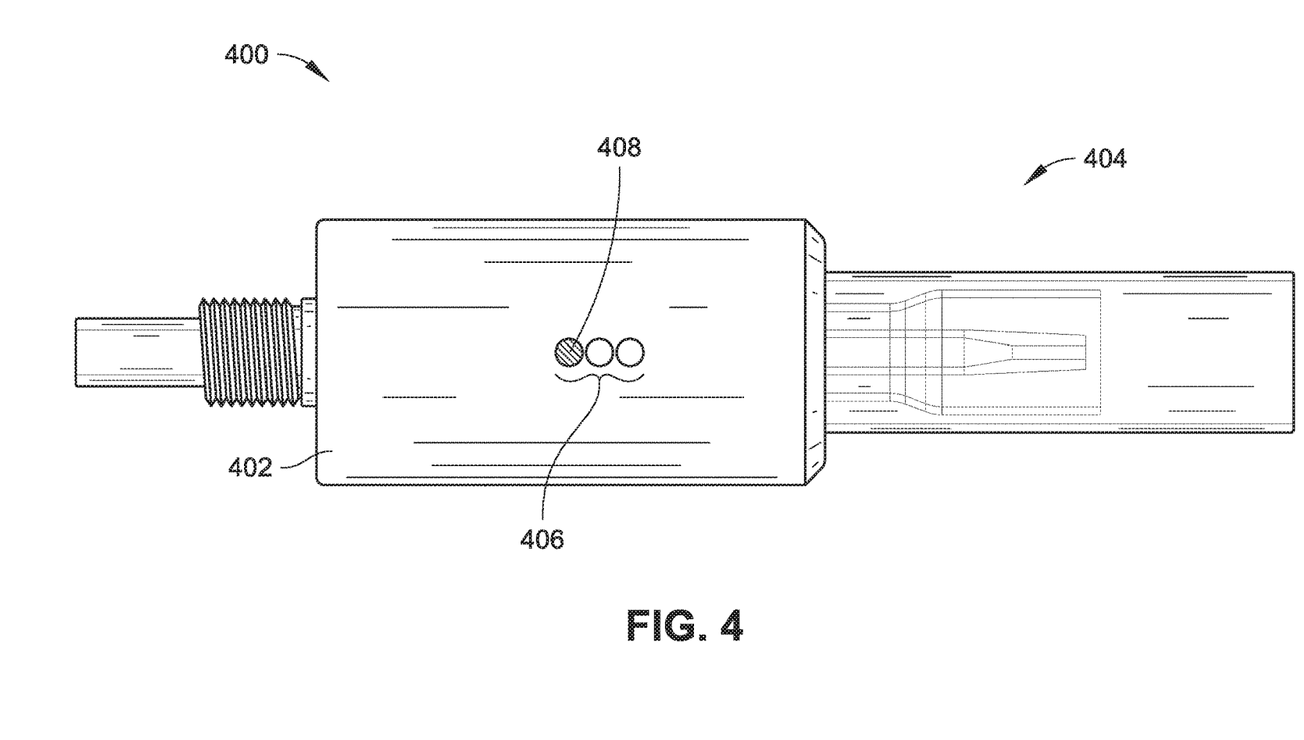
FIG. 4 is a side view of a sample introduction system component including a visual marking in accordance with an example embodiment of the present disclosure.

FIGS. 2A through 2C illustrate a plurality of sample introduction system components 110 that are physically associated with respective exchangeable mounting structures 102 in accordance with example embodiments of the present disclosure. Each of the exchangeable mounting structures 102 shown are coupled with and physically associated with a spray chamber (spray chambers 108A, 108B, 108C are shown), an injector (injectors 106A, 106B, 106C are shown), and a torch (torches 104A, 104C are shown), where the exchangeable mounting structures 102 and the sample introduction system components 110 have at least one matching visual marking or coloring. The exchangeable mounting structures 102 can also support additional or alternative sample introduction system components 110 including, but not limited to, nebulizers (nebulizer 300 is shown in FIGS. 3A and 3B), fluid connections (e.g., ports for coupling components, gas tubing, liquid tubing, multiposition valves, flow-through valves, etc.), and pump systems. In an implementation, with reference to FIG. 2A, the spray chamber 108A includes a marking band 116A having a first color (e.g., brown) positioned around an outlet 118A of the spray chamber 108A. The marking band 116A matches the visual marking or coloring (e.g., brown) of the exchangeable mounting structure 102A to associate the two components as being designed to be utilized together for a particular analysis in the ICP or ICPMS instrument 10. The spray chamber 108A is secured to a coupler 120A having a marking band 122A that also matches the visual marking or coloring (e.g., brown) of the exchangeable mounting structure 102A to visually associate components as being designed to be utilized together for a particular analysis in the ICP or ICPMS instrument 10. The coupler 122A can secure the injector 106A relative to the spray chamber 108A through the exchangeable mounting structure 102A, where the marking band 122A can provide a visual marking or color for the injector 106A. The torch 104A also includes a marking band 124A that matches the visual marking or coloring (e.g., brown) of each of the marking bands 116A and 122A and of the exchangeable mounting structure 102A to visually associate all the respective components as being designed to be utilized together for a particular analysis in the ICP or ICPMS instrument 10.

While marking bands 116A, 122A, and 124A are shown, the visual marking or coloring of the sample introduction system components 110 (or the exchangeable mounting structure 102) can differ from a band. In implementations, the sample introduction system components 110 can include a marker received within an aperture in the sample introduction system components 110. For example, with reference to FIGS. 3A and 3B, the nebulizer 300 includes a marking rod 302 having a visual marking or coloring (e.g., green) to visually associate the nebulizer with other components (e.g., spray chamber 108B, exchangeable mounting structure 102B, etc.) as being designed to be utilized together for a particular analysis in the ICP or ICPMS instrument 10. The marking rod 302 is received into an aperture 304 in the nebulizer 300 to secure the marking rod 302 in place. In implementations, the marking rod 302 is received into the aperture 304 and secured in place via friction fit, however an adhesive or other material can be used to secure the marking rod 302 within the aperture 304. As another example of a visual marking or coloring, with reference to FIG. 4, a torch assembly 400 includes a torch body 402 coupled to torch tubes 404. The torch body 402 includes a visual marking 406 having a pattern of three circles, with a first circle 408 having a particular color (e.g., blue) to associate the torch assembly 400 with additional system components (e.g., spray chamber 108C, exchangeable mounting structure 102C, etc.) as being designed to be utilized together for a particular analysis in the ICP or ICPMS instrument 10.

In implementations, the exchangeable mounting structures 102 and/or the sample introduction system components 110 can include a plurality of visual markings or colorings when the exchangeable mounting structures 102 and/or the sample introduction system components 110 can be utilized with a plurality of components for differing analyses in the ICP or ICPMS instrument 10. For example, where a torch can be utilized for multiple analyses with an ICP or ICPMS instrument (and thus be physically associated with differing sample introduction system components 100 and/or exchangeable mounting structures 102), the torch can be provided with a plurality of visual markings or colorings. For instance, with reference to FIG. 2A, the system 100 includes the spray chamber 108A having a first (e.g., brown) coloring or marking via the marking band 116A, the coupler 120A having the first (e.g., brown) coloring or marking via the marking band 122A, the exchangeable mounting structure 102A having the first (e.g., brown) coloring or marking, and the torch 104A having both the first (e.g., brown) coloring or marking via the marking band 124A and a second (e.g., green) coloring or marking via a marking band 126A. With reference to FIG. 2B, the system 100 includes the spray chamber 108B having the second (e.g., green) coloring or marking via a marking band 116B, a coupler 120B having the second (e.g., green) coloring or marking via a marking band 122B, the exchangeable mounting structure 102B having the second (e.g., green) coloring or marking, and the torch 104A having both the first (e.g., brown) coloring or marking via the marking band 124A and the second (e.g., green) coloring or marking via the marking band 126A. Thus, the torch 104A shown in the systems 100 of FIGS. 2A and 2B can be physically associated with each of the exchangeable mounting structure 102A having the first (e.g., brown) coloring or marking and the exchangeable mounting structure 102B having the second (e.g., green) coloring or marking. As further shown in FIG. 2C, the system 100 includes the spray chamber 108C having a third (e.g., blue) coloring or marking via a marking band 116C, a coupler 120C having the third (e.g., blue) coloring or marking via the marking band 122C, the exchangeable mounting structure 102C having the third (e.g., blue) coloring or marking, and a torch 104C having both the third (e.g., blue) coloring or marking via the marking band 124C and the second (e.g., green) coloring or marking via the marking band 126A. In implementations, the matching coloring or markings can facilitate assembly of the exchangeable mounting structures 102 with the respective sample introduction system components 110, such as to ensure that the proper sample introduction system components 110 are physically associated with each other to perform a specific analysis, where non-matching sample introduction system components 110 could introduce error to the analysis by introducing physical characteristics that are undesirable when performing the analysis. For example, the spray chamber 108C would be incompatible with the exchangeable mounting structures 102A or 102B, the torch 104A (associated with marking bands 124A and 126A), and the injector 106A (associated with marking band 122A).

Figure 5:
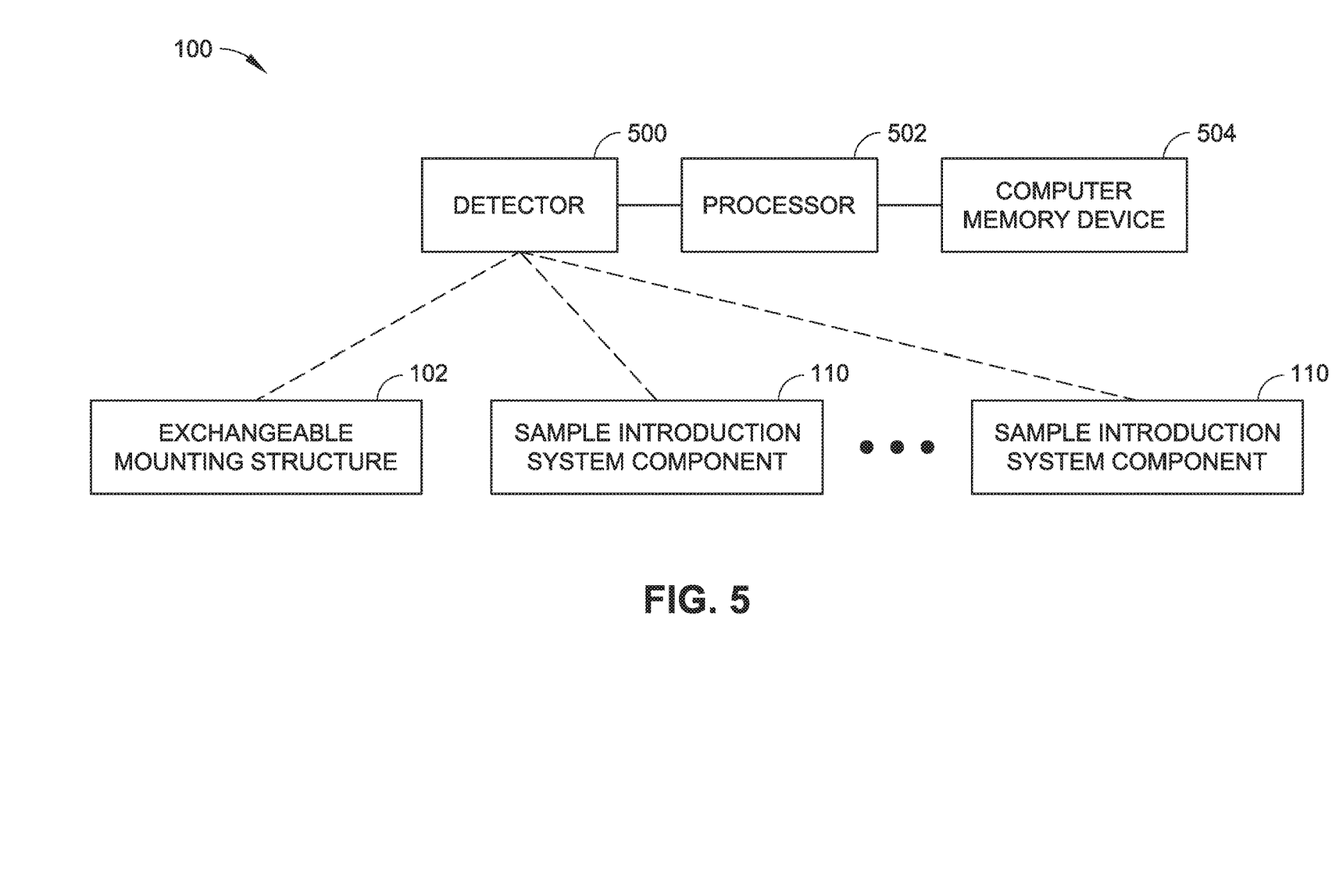
FIG. 5 is a schematic diagram of a system for managing differing sample introduction system components with respect to a mounting structure for ICP and ICPMS instruments in accordance with an example embodiment of the present disclosure.

In implementations, the marking associated with an exchangeable mounting structure 102 or a sample introduction system component 110 can include characteristics distinct from or in addition to coloring. Multiple variations of markings can be utilized to provide redundancy in verifying that the exchangeable mounting structure 102 is physically associated with the sample introduction system components. For example, in implementations, the marking includes one or more of a barcode (e.g., a 2-dimensional (2-D) or matrix barcode), a letter, a number, a symbol, an alphanumeric character, a surface texturing, and the like. The marking can include an identifying code configured to be detected and recognized by a detector. For example, in implementations, the marking can include one or more of an RFID chip, a barcode, a magnetic or physical pattern, and the like. With reference to FIG. 5, the system 100 can include a detector 500 configured to identify the exchangeable mounting structures 102 and the sample introduction system components 110 based on the marking and/or color associations (e.g., based on a marking band, marking rod, surface coloration, and the like). In implementations, the detector 500 includes an optical sensor, such as a camera, light sensor, and the like, a contact sensor, a conductivity sensor, and so on. The detector 500 can be incorporated into one or more of the exchangeable mounting structure 102, the ICP or ICPMS instrument 10, or other location. The detector 500 can detect the presence of the exchangeable mounting structure 102 and the sample introduction system components 110 based on the marking and/or color associations and compare the respective exchangeable mounting structure 102 and the sample introduction system components 110 (e.g., via a processor 502 or controller operably coupled to or integrated with the detector 500, or otherwise included in the system 100) to determine whether the appropriate exchangeable mounting structure 102 and/or the sample introduction system components 110 are mounted to the ICP or ICPMS instrument 10 for a particular sample analysis. For example, in an implementation, the processor 502 compares the output from the detector 500 related to the color and/or marking of the exchangeable mounting structure 102 and the sample introduction system components 110 mounted thereto and compares the output against data stored in a computer memory device 504 to verify that the exchangeable mounting structure 102 measured by the detector 500 and each sample introduction system component 110 mounted thereto are associated with a scheduled sample analysis. The computer memory device 504 can store data associated with a sample analysis, the components required for a particular sample analysis, and a list of approved exchangeable mounting structures 102 and approved sample introduction system components 110 for the particular sample analysis. The system 100 can provide an alert when a particular sample introduction system component 110 or exchangeable mounting structure 102 does not match the approved component list for a given sample analysis scheduled to run on the ICP or ICPMS instrument 10. For example, the processor 502 can initiate an alert via a display device associated with the system 100. The alert can include a recommendation regarding which component to change (e.g., exchange a blue type injector for a green type injector) to provide an associated set of the exchangeable mounting structure 102 and the sample introduction system components 110 mounted thereto. The system 100 can also provide an indication regarding which sample analysis or analyses would be appropriate given the identified sample introduction system components 110 and exchangeable mounting structure 102. For example, the computer memory device 504 can store a data set (e.g., one or more indexes or tables) of particular sample analyses and the associated exchangeable mounting structures 102 and the sample introduction system components 110 appropriate for the particular sample analyses. The processor 502 can compare the system components identified by the detector 500 to the particular groupings provided for in the one or more indexes or tables and display the sample analyses, if any, that correspond to the identified system components. The alerts and other information displayed (e.g., which sample analyses are appropriate for the currently installed system components) can provide an operator an indication that the currently mounted exchangeable mounting structure 102 and sample introduction system components 110 may not be compatible with a desired sample analysis.

The processor 502 provides processing functionality for the system 100, such as for analysis of operations by the detector 500, and can include any number of processors, micro-controllers, or other processing systems, and resident or external memory for storing data and other information accessed or generated by the detector 500. The processor 502 can execute one or more software programs that implement techniques described herein. The processor 502 is not limited by the materials from which it is formed or the processing mechanisms employed therein and, as such, can be implemented via semiconductor(s) and/or transistors (e.g., using electronic integrated circuit (IC) components), and so forth. The computer memory device 504 is an example of tangible, computer-readable storage medium that provides storage functionality to store various data associated with operation of the system 100, such as software programs and/or code segments, or other data to instruct the processor 502, and possibly other components of the detector 500, to perform the functionality described herein. Thus, the computer memory device 504 can store data, such as a program of instructions for operating the system 100 (including its components), and so forth. It should be noted that while a single memory is described, a wide variety of types and combinations of memory (e.g., tangible, non-transitory memory) can be employed. The computer memory device 504 can be integral with the processor 502, can comprise stand-alone memory, or can be a combination of both. The computer memory device 504 can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 100 and/or the computer memory device 504 can include removable integrated circuit card (ICC) memory, such as computer memory device 504 provided by a subscriber identity module (SIM) card, a universal subscriber identity module (USIM) card, a universal integrated circuit card (UICC), and so on.

The system 100 can include a physical keying arrangement between an exchangeable mounting structure 102 and respective sample introduction system component(s) 110 to provide a physical barrier that prevents mounting of the sample introduction system components 110 that do not match the particular physical keying arrangement of the exchangeable mounting structure 102. For example, in an implementation, the system 100 includes an exchangeable mounting structure 102 having a physical key component arranged therewith and at least one physically associated sample introduction system component 110 having a corresponding physical key component configured to at least one of mate with or match the physical key component of the exchangeable mounting structure 102. The physical key component can include, but is not limited to, a physical protrusion, a recess, a combination thereof, and the like.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system comprising:
    a mount having at least one of a visual marking or a coloring, the mount configured to couple with an inductively coupled plasma analytical instrument;
    a physically associated sample introduction system component having at least one of a visual mark or a coloring matching the at least one of a visual marking or a coloring of the mount, wherein the at least one of a visual marking or a coloring corresponds to a sample analysis configuration for analyzing a particular sample type at the inductively coupled plasma analytical instrument;
    a detector operably coupled to the mount and the physically associated sample introduction system component, the detector configured to detect the at least one of a visual marking or a coloring of the mount and the at least one of a visual mark or a coloring of the physically associated sample introduction system component; and
    a processor operably coupled to the detector, the processor configured to receive an output from the detector associated with the detected at least one of a visual marking or a coloring of the mount and the detected at least one of a visual mark or a coloring of the physically associated sample introduction system component and to compare the output of the detector to a data set including a component list corresponding to one or more sample analysis configurations.

2. The system of claim 1, further comprising:
    a second sample introduction system component having at least one of a visual mark or a coloring that differs the at least one of a visual mark or a coloring of the physically associated sample introduction system component, the at least one of a visual mark or a coloring of the second sample introduction system component corresponding to a second sample analysis configuration for analyzing a second sample type at the inductively coupled plasma analytical instrument.

3. The system of claim 1, further comprising:
    a second sample introduction system component having at least one of a visual mark or a coloring that matches the at least one of a visual marking or a coloring of the mount.

4. The system of claim 1, wherein the physically associated sample introduction system component includes a first visual mark or coloring and a second visual mark or coloring, the first visual mark or coloring matching the at least one of a visual marking or a coloring of the mount and corresponding to a first sample analysis configuration at the inductively coupled plasma analytical instrument, the second visual mark or coloring differing from the at least one of a visual marking or a coloring of the mount and corresponding to a second sample analysis configuration at the inductively coupled plasma analytical instrument.

5. The system of claim 1, wherein the physically associated sample introduction system component includes at least one of a spray chamber, a torch, an injector, or a nebulizer.

6. The system of claim 1, wherein the at least one of a visual mark or a coloring of the physically associated sample introduction system component includes a marking band having a first color.

7. The system of claim 1, wherein the at least one of a visual mark or a coloring of the physically associated sample introduction system component includes a marker having a first color, the physically associated sample introduction system component further defining an aperture to receive at least a portion of the marker.

8. The system of claim 1, wherein the detector includes at least one of an optical sensor, a contact sensor, or a conductivity sensor.

9. The system of claim 1, wherein the processor initiates an alert responsive to comparison of the output of the detector to the data set.

10. The system of claim 9, wherein the alert includes a notification that one or more of the mount or the physically associated sample introduction system component is not included in the component list for a sample analysis scheduled for the inductively coupled plasma analytical instrument.

11. The system of claim 9, wherein the alert includes a recommendation to replace one or more of the mount or the physically associated sample introduction system component.

12. The system of claim 9, wherein the alert includes a recommendation of which sample type to analyze at the inductively coupled plasma analytical instrument.

13. A method comprising:
    introducing at least one of a visual marking or a coloring to a mount, the mount configured to couple with an inductively coupled plasma analytical instrument;
    introducing at least one of a visual mark or a coloring to a physically associated sample introduction system component that matches the at least one of a visual marking or a coloring of the mount; and
    storing in a computer memory an association between the at least one of a visual marking or a coloring and a sample analysis configuration for analyzing a particular sample type at the inductively coupled plasma analytical instrument.

14. The method of claim 13, further comprising:
    detecting the at least one of a visual marking or a coloring of the mount and the at least one of a visual mark or a coloring of the physically associated sample introduction system component.

15. The method of claim 14, further comprising:
    comparing the detected at least one of a visual marking or a coloring of the mount and the detected at least one of a visual mark or a coloring of the physically associated sample introduction system component to a data set including a component list corresponding to one or more sample analysis configurations; and
    displaying a notification that one or more of the mount or the physically associated sample introduction system component is not included in the component list for a sample analysis scheduled for the inductively coupled plasma analytical instrument.

16. The method of claim 14, further comprising:
    displaying a recommendation to replace one or more of the mount or the physically associated sample introduction system component.

17. The method of claim 14, further comprising:
displaying a recommendation of which sample type to analyze at the inductively coupled plasma analytical instrument.

18. The method of claim 13, further comprising:
detecting the at least one of a visual marking or a coloring of the mount and the at least one of a visual mark or a coloring of the physically associated sample introduction system component when the mount is coupled to the inductively coupled plasma analytical instrument.

* * * * *